United States Patent
Gunn et al.

(10) Patent No.: US 8,884,215 B2
(45) Date of Patent: Nov. 11, 2014

(54) METHOD AND APPARATUS FOR ANALYZING COMPOSITION OF HYDROCARBON AND CARBON DIOXIDE GASES LIBERATED FROM DRILLING FLUIDS

(71) Applicant: Stephen Paul Krupp, Lake Jackson, TX (US)

(72) Inventors: Scott Edwin Gunn, Calgary (CA); John Wesley DeBliek, Calgary (CA)

(73) Assignee: Geological Rentals & Services, Inc., Calgary, AB (CA)

( * ) Notice: Subject to any disclaimer, the term of this patent is extended or adjusted under 35 U.S.C. 154(b) by 0 days.

(21) Appl. No.: 13/918,791

(22) Filed: Jun. 14, 2013

(65) Prior Publication Data
US 2013/0334412 A1    Dec. 19, 2013

Related U.S. Application Data

(60) Provisional application No. 61/660,198, filed on Jun. 15, 2012.

(51) Int. Cl.
| | |
|---|---|
| *G01V 5/08* | (2006.01) |
| *G01V 5/00* | (2006.01) |
| *E21B 47/00* | (2012.01) |
| *G01N 33/24* | (2006.01) |
| *G01N 33/28* | (2006.01) |

(52) U.S. Cl.
CPC .................................. *G01N 33/2823* (2013.01)
USPC ..... 250/269.1; 250/255; 250/253; 73/152.01; 436/30

(58) Field of Classification Search
USPC ............................................... 250/255, 269.1
See application file for complete search history.

(56) References Cited

U.S. PATENT DOCUMENTS

| | | | |
|---|---|---|---|
| 2,500,213 A * | 3/1950 | Stevens ......................... 250/255 |
| 5,473,162 A * | 12/1995 | Busch et al. ................ 250/341.6 |
| 2004/0178336 A1 | 9/2004 | DiFoggio et al. | |
| 2005/0269499 A1* | 12/2005 | Jones et al. ................. 250/269.1 |
| 2006/0202122 A1 | 9/2006 | Gunn et al. | |
| 2008/0030729 A1* | 2/2008 | DiFoggio ...................... 356/328 |
| 2008/0078544 A1* | 4/2008 | Christian et al. .............. 166/264 |
| 2009/0008560 A1* | 1/2009 | Gunn et al. .................... 250/343 |
| 2011/0313670 A1* | 12/2011 | DeGreeve et al. .............. 702/13 |

FOREIGN PATENT DOCUMENTS

WO    2011146068    11/2011

\* cited by examiner

*Primary Examiner* — David Porta
*Assistant Examiner* — Jeremy S Valentiner
(74) *Attorney, Agent, or Firm* — Law Office of Stephen P. Krupp, PLLC (57) ABSTRACT

In various embodiments is described a device and method for rapidly analyzing compositions of gases liberated from drilling fluid using spectral absorption analysis. Specifically the invention describes flowing the sample gas thru a closed path gas cell, irradiating the sample gas with a wide band infrared emitter in the 2 to 5 μm wavelength range, measuring the infrared absorbance spectrum in the range of 2 to 5 μm using a spectrometer and determining the composition of the gas sample using multivariate analysis of the spectrum. The composition includes the concentration of any one or more, either singularly or in combination, of hydrocarbon gases containing one to eight carbon atoms and carbon dioxide gas.

11 Claims, 9 Drawing Sheets

METHOD AND APPARATUS FOR ANALYZING COMPOSITION OF HYDROCARBON AND CARBON DIOXIDE GASES LIBERATED FROM DRILLING FLUIDS

CROSS REFERENCE TO RELATED APPLICATIONS

This application claims priority from U.S. Provisional Patent Application Ser. No. 61/660,198 filed Jun. 15, 2012, and for purpose of United States patent application practice, the disclosure of which is incorporated herein by reference.

FIELD

The present disclosure relates to a device for analyzing hydrocarbon gas content of drilling mud. The invention also relates to a method of detecting, analyzing and quantifying the composition of hydrocarbon gases liberated from the drilling mud.

BACKGROUND

During a drilling operation, drilling fluid (or "mud") is continuously pumped down through the drill string, through the mud motor if directional drilling, out through the drill bit and then back up a borehole annulus to the surface. Often the mud is made up of clays, chemical additives and an oil or water base and performs several important functions. The primary function of the mud is to cool and lubricate the drill bit. Other functions of the mud are to carry drill cuttings back up out of the well and maintain a hydrostatic pressure which prevents pressurized fluids in the earth formation from blowing out through the well borehole. When the drill bit drills thru rock formations it may encounter hydrocarbons entrapped in that formation. Therefore the drilling fluid performs an important secondary function by carrying hydrocarbon information back to the surface about the nature of the formation being penetrated.

As the drilling fluid returns to the surface these liberated hydrocarbon gases are released by direct agitation with a gas trap and a gas sample is drawn by a gas chromatograph. By examining the quantity and type of gas released the petroleum geologist and/or mudlogger may determine how feasible it is to obtain oil and/or gas from the well. This information can indicate to the geologist and/or mudlogger that they are on the correct well path in targeting the zone of interest or give indications that they have drilled out of targeted zone of interest. The longer the time a drill bit has drilled out of a targeted zone the less productive pay zone will be achieved. Current day drilling rig rate of penetrations have increased significantly to previous years rate of penetration due to advancements in drill bit technology, mud motors and drill fluids. Even horizontal wells rates of penetration have greatly increased.

Current gas chromatograph equipment take a spot sample of the liberated gases, but require up to 5 minutes and analyze the sample. While the sample is being analyzed over this time period other gas samples go by unanalyzed resulting in missing valuable information about the formation. Previous gas chromatography have been an instrumental method used for the separation and identification of chemical compounds and gases, but are a slow process as every component of gas moves through the column at a different rate to be analyzed. The time cycle required to separate and then analyze the hydrocarbons can take up to 5 minutes for full breakdown (methane to octane). Newer high speed chromatographs can provide data on the hydrocarbon spectra (methane to Butanes) in around 1 minute, but do not provide any data on the heavier hydrocarbons (pentane to octane). These heavier hydrocarbons (pentane to octane) are required to calculate proper gas ratio formulas to predict the hydrocarbon state. Also, many current gas chromatographs require a carrier gas such as helium to burn the detector at a consistent heat level and may also require an operator to ensure the gas chromatograph operates properly adding more cost to drilling operations. When using a combustion type detector in a gas chromatograph any amount of nitrogen and/or carbon dioxide will give a false reading in a gas chromatograph affecting the hydrocarbon response.

U.S. Pat. No. 7,741,605 discloses a mud logging gas detector using NDIR gas detector technology. The gas detector used 4 NDIR channels based on custom filter ranges in the mid infrared range to provide two gas concentration readings, one for Methane and one labeled as Propane which includes the heavier hydrocarbon gases from Ethane and up. Due to the overlap between the absorption spectra of the hydrocarbon gases, NDIR sensors cannot provide good separation of the gas components.

US Publication 2011/0313670 uses a type of spectrometer in the near infrared (IR) region rather than the mid IR. US Publication 2011/0313670 monitors a near IR hydrocarbon absorption region around 1.55-1.85 µm. However, near IR absorption band is roughly 3 orders of magnitude less sensitive than the primary band in the mid IR. In this portion of the near IR spectrum only one absorption band is available. This reduces the spectral information available for use in the analysis of the gas composition compared to using a broader spectral region such as the 2.0 to 5.0 µm mid IR range.

Accordingly, there is a need for a more reliable apparatus for identifying constituents of sample gas from drilling mud in a much quicker time frame to keep up with the increased drilling rate of penetration. In particular, there is need to distinguish one or more hydrocarbon types containing one to eight carbon atoms, such as methane, ethane, propane, butane isomers (n-butane, iso-butane), pentane isomers (n-pentane, iso-pentane, neo-pentane), hexane isomers (hexane, methyl-pentanes, dimethylbutanes), heptanes, and octanes, and carbon dioxide gas carried by the drilling fluid returning from a well, and to provide an indication of how much of those gases are present, if any. There is a need to provide said gas data at a quicker interval then current industry gas chromatographs to be able to react most effectively to changing hydrocarbon gases and ratios and hence maximize targeted zones and well production.

Furthermore, it would be desirable if such apparatus were lighter and less bulky than prior apparatus and did not include the expense of requiring an operator skilled in spectroscopic analysis to be on the rig site.

SUMMARY

We have discovered that using a high resolution spectrometer to generate a full spectral plot of the absorption spectrum (hundreds of channels), versus four comparatively broad channels using narrow band filters, and the use of multivariate techniques to isolate the individual gases in a way that is not physically possible with a NDIR curve fitting calibration, allows isolation of each gas component from C1 to C5 (iso and normal for C4 and C5 to make 7 components) in a comparable fashion to a gas chromatograph (GC).

One embodiment of this invention is a device that analyzes the composition of hydrocarbon gases comprising one to eight carbons released from drilling muds, wherein the device comprises a wide band infrared emitter, a gas cell in which the sample gas is irradiated, a spectrometer, a focusing optic element that directs gas cell radiation into the spectrometer, and a system processor that performs analysis of the absorption spectrum to determine the gas composition, preferably further comprising a non-combustion type detector. The device can further comprise a strip recorder, preferably linked to a computer. The device can also further comprise software that analyzes hydrocarbon gas and carbon dioxide compositions and assists drilling decisions.

The device analyzes hydrocarbon gases comprising one to five carbons, more preferably one to eight carbons released from drilling muds at least once every 10 seconds, more preferably at least once every 2 seconds.

The device is also light weight and has a small footprint (space area which it occupies). The device has at least about 10 percent or more smaller footprint or at least about 10 percent lighter weight than devices using combustion type devices. The device also can be at least about 10 percent lighter weight than devices using combustion type devices.

The device can further comprise an integrated data communication device for off-site monitoring. The device can further comprise a spectrometer having a spectral resolution of 40 nm or less, more preferably 20 nm or less, and most preferably less than 10 nm within the 2.0 to 5.0 µm range.

Another embodiment of the invention is a method of detecting, analyzing and quantifying the composition of hydrocarbon gases liberated from the drilling mud of a oil and/or gas well using multi-channel infrared spectral analysis of the sample gases, the method comprising: (a) liberating gases from drilling mud to form a gas sample; (b) drawing the sample into a gas measurement cell using an electromechanical pump; (c) irradiating the gas sample with infrared radiation from a wide band source covering a range of at least 2.0 to 5.0 micrometers; (d) using a multichannel spectrometer to measure the absorption spectrum of the sample gas based on comparison to a reference spectrum; (e) using a system processor to perform multivariate analysis of the absorption spectrum allowing the sample gas hydrocarbon composition to be analyzed and quantified.

The method can further comprise simultaneously measuring hydrocarbon gases comprising one to eight carbons present in drilling muds, especially in the presence of carbon dioxide.

The method for rapid analysis of hydrocarbon gases comprising one to eight carbons present in drilling muds in the presence of carbon dioxide of the invention is especially useful wherein the detectable concentration range of combined hydrocarbon gases is at least about 100 ppm to 100 percent concentration by volume.

The method for rapid analysis of hydrocarbon gases comprising one to eight carbons present in drilling muds of the invention is also useful wherein the detectable carbon dioxide concentration is at least about 100 ppm to about 10 percent concentration by volume in the presence of the hydrocarbon gases.

BRIEF DESCRIPTION OF THE DRAWINGS

FIG. 11 illustrates a drilling rig that has drilled horizontally to target a gas producing formation such as point (23). Due to longer gas chromatographs sample analysis time intervals the drilling continued out of the gas bearing formation at point (24) and into a non-producing formation. Not until the next gas chromatograph sample analysis is available can the geologist and/or mudlogger adjust the directional drilling of the wellpath to geosteer back down into the targeted formation at point (25). With 70 percent of current day wells being drilled horizontally or directionally, the geologist and/or mudlogger would benefit from a faster indication of the need to adjust the drill bit's well path or rate of penetration to maximize the targeted hydrocarbon zone and potential production.

DETAILED DESCRIPTION

This invention is primarily a method of analysing composition of gas liberated from drilling mud in oil and gas well drilling applications, also known as mud logging. Gas analysis is performed based on infrared absorption characteristics of the gases in the mid infrared spectral range (2.0 to 5 µm). Analysis involves determination of the total concentration and relative ratios of hydrocarbon gases and carbon dioxide in the gas sample. Typical hydrocarbon gases being analysed may include methane, ethane, propane, butane isomers (n-butane, isobutane), pentane isomers (n-pentane, isopentane, neopentane), hexane isomers (hexane, methylpentanes, dimethylbutanes), heptane isomers, and octane isomers. Mixtures of these gases are usually present so it is necessary to distinguish between them for analysis of the overall gas composition. Thus Analysis of the hydrocarbon gases may involve determining concentrations of individual gases and/or combinations of gases and determining relative ratios of the gases and analysis of the hydrocarbon gases can cover a wide concentration range, typically from around 10 ppm to 100% of total hydrocarbon gas concentration by volume. However, analysis of carbon dioxide concentration covers a range from less than 100 ppm to 10% concentration by volume in the presence of the hydrocarbon gases.

A wide band infrared emitter is used to generate radiation in the 2.0 to 5 µm range for the analysis of the hydrocarbon gases. The radiation from the emitter is collimated and passed through the sample gas within a closed path gas cell. The Infrared absorption spectrum of the sample gas is measured using a spectrometer covering the 2.0 to 5 µm spectral range.

A higher number of spectral channels can be beneficial in helping to isolate the individual gas components provided the signal to noise ratio is high enough. Covering multiple absorption regions of the hydrocarbons is also beneficial as it provides more information that can be used for calibration and it provides multiple absorbance levels for the gases, so that as the gas concentrations vary, the best portion of the spectrum can be used for analysis within a certain range of concentration. In this way the strongest absorption region is used for low concentrations, and as the gas concentrations increase, saturated portions of the spectrum are removed from the analysis and lower absorption regions of the spectrum are added to the analysis.

FTIR spectrometers can also provide relatively high resolution outputs with low noise, but have historically been large, expensive and not rugged enough for field use. Newer devices such as the FTIR rocket (available from Arcoptix) provide good spectral resolution (over 700 channels in 2-5 µm range) in a small, rugged package and can be used in the invention described herein.

The multi-channel spectral data generated by the spectrometer is analysed using multivariate techniques such as partial least squares regression or support vector regression in order to determine the gas concentrations and ratios. Multivariate analysis is commonly used to process overlapping or highly correlated data such as the overlapping absorption bands of the hydrocarbon gases. A calibration gas set is used such that the concentrations and relative gas ratios can be varied over the expected nominal operational range (based on accepted ranges of the wetness, balance and character ratios). In concentration, this range is from tens of ppm total Hydrocarbon gas up to 100 percent by volume. Individually, the ranges of the gases are typically 0-100 percent C1 (methane), 0-20 percent C2 (ethane), 0-20 percent C3 (propane), 0-5 percent normal and iso C4 (butane), 0-3 percent normal and iso C5 (pentane), and less than 1 percent for all other components.

Multivariate analysis software such as Unscrambler by Camo is used to analyze and generate calibration models for each gas or combination of gases being calibrated for. Prediction software such as the Unscrambler online predictor is used to analyze data coming from the spectrometer in real time and use the calibration models to predict the gas concentration levels. Prediction values can be generated much faster than a gas chromatograph, with a sample period within a range of 1 to 10 seconds depending on processing and averaging selections. Additional processing of the spectral data such as baseline shift removal via derivatives and reference spectrum tracking also help improve the quality of the predicted gas concentrations.

Figure 4:
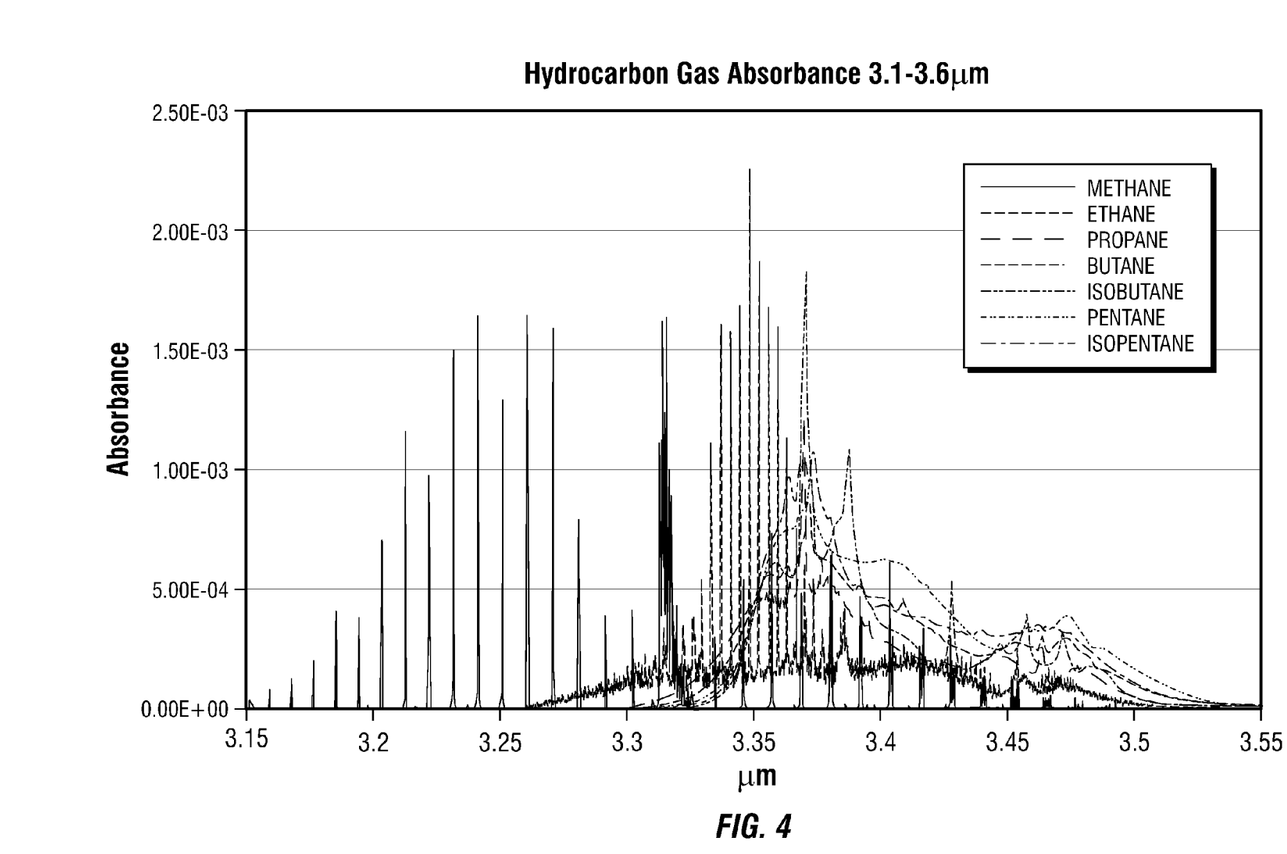
FIG. 4 shows a Spectral Data Chart of the Primary Hydrocarbon Infrared Absorbance Region 3.1-3.6 µm.
Figure 5:
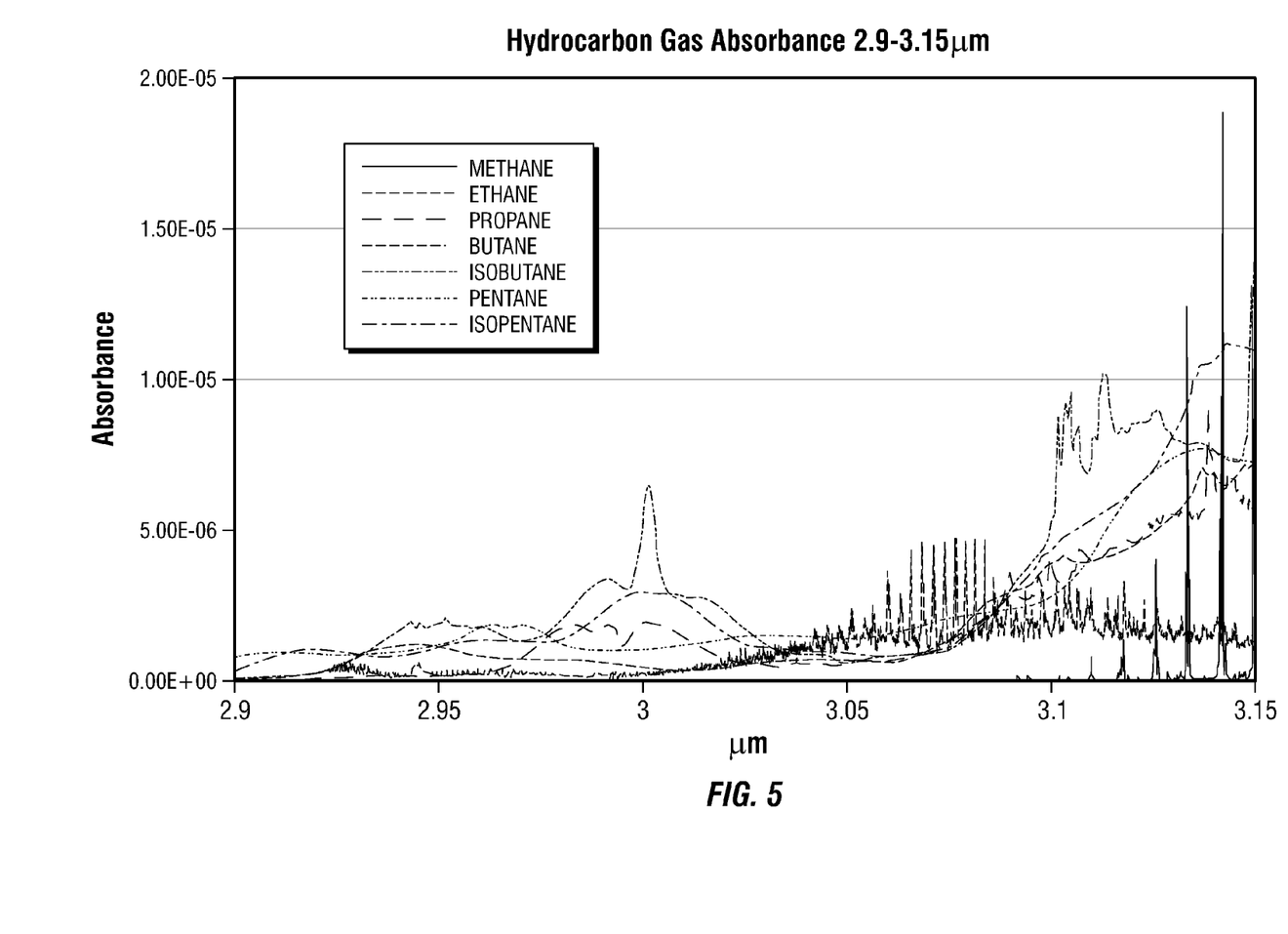
FIG. 5 shows a Spectral Data Chart of the lower shoulder Hydrocarbon Infrared Absorbance Region 2.9-3.15 µm.
Figure 6:
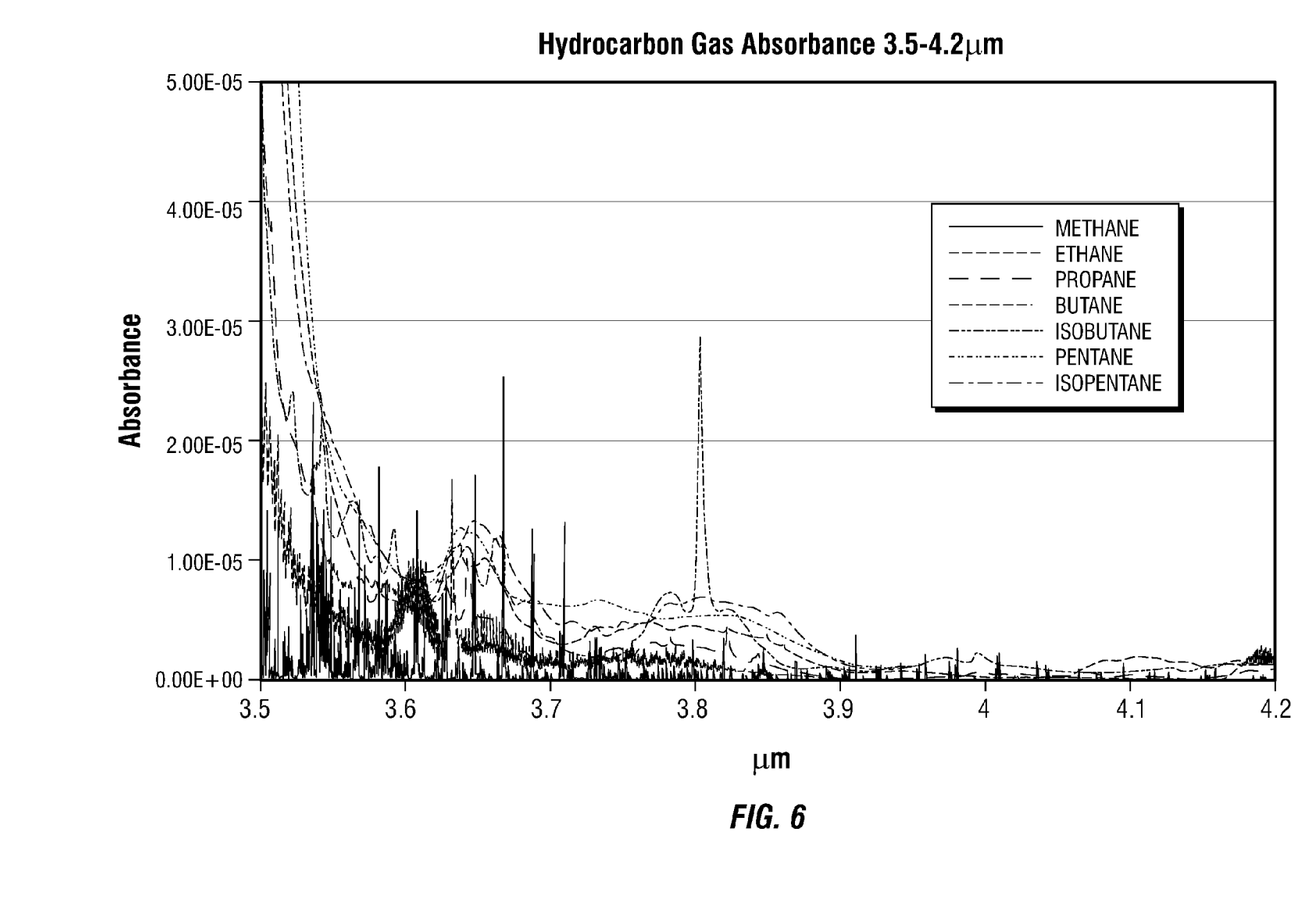
FIG. 6 shows a Spectral Data Chart of the upper shoulder Hydrocarbon Infrared Absorbance Region 3.5-4.2 µm.

The 2.0-5.0 µm spectral range is used as it contains the primary hydrocarbon absorption band and a lower secondary absorption band as well as the primary and secondary carbon dioxide absorption bands. This allows different portions of the spectrum to be used based on concentrations being detected. For instance, the primary absorption band has the highest absorption in the entire infrared spectrum, making it ideal for detecting low concentrations of hydrocarbons. However as the concentration rises this band will start to saturate and higher concentrations will not be detectable. Then by moving to the lower absorbance shoulder and secondary spectral regions, the detectable range can be increased to cover higher concentrations of hydrocarbons. The primary hydrocarbon absorption band is in the 3.1-3.6 µm spectral region as shown in FIG. 4. In order to detect the full concentration range of hydrocarbon gases, the sample gas path length is set such that the primary absorption band is used at low concentrations and once this region starts to saturate, lower absorbance regions on either side of the primary band and the secondary absorption region shown in FIG. 6 may be used to detect higher concentrations. The lower absorbance 'shoulder' regions of the hydrocarbon gases are shown in FIGS. 4 and 5. The secondary absorption region is shown in FIG. 6. The primary absorption band for carbon dioxide is used for measurement of lower concentrations of carbon dioxide. The primary absorption band for carbon dioxide is in the 4.2-4.4 µm spectral range as shown in FIG. 4. The secondary carbon dioxide absorption band lies in the 2.6-2.8 µm spectral region as shown in FIG. 5. This part of the spectrum can be utilized for higher concentrations of carbon dioxide when the primary band saturates.

Described herein are a method and apparatus for analyzing composition of a gas sample that is conveyed in a drilling fluid (or drilling mud) of an Oil and Gas well drilling rig application known as MudLogging. Following which it is irradiated with infrared radiation in the mid-infrared range.

Gas analysis is performed based on infrared absorption characteristics of the gases in the mid infrared spectral range 2 to 5 µm. The gases to be analysed are hydrocarbon gases which may contain one or more hydrocarbons containing one to eight carbon atoms, such as methane, ethane, propane, butane isomers (n-butane, iso-butane), pentane isomers (n-pentane, iso-pentane, neo-pentane), hexane isomers (methylpentanes, dimethylbutanes), heptanes, and octanes and carbon dioxide gas.

A wide band infrared emitter is used to generate radiation in the 2 to 5 µm range. The infrared light source is shown on FIG. 3. The radiation from the emitter is collimated and passed through the sample gas inlet within a closed path gas cell. The Infrared absorption spectrum of the sample gas is measured using an Infrared Spectrometer covering the 2 to 5 µm spectral range.

The spectrometer may be any device which can measure the relative infrared intensity over multiple contiguous spectral channels covering the 2 to 5.0 µm region of the mid-infrared spectrum. Within certain limits, a higher number of spectral channels will allow more detailed analysis of the gases provided there is adequate signal to noise. The spectral resolution should be better than 40 nm, more preferably better than 20 nm, most preferably better than 10 nm Since the IR Rocket resolution is constant in wavenumbers rather than wavelength, its resolution ranges from under 2 nm at 2 µm, up to 10 nm at 5 µm.

The present invention also provides the ability to isolate gases with 1 to 5 carbons in the presence of gases with higher numbers of carbon, more preferably gases with 1 to 8 carbons in the presence of gases with higher numbers of carbons. This would then indicate the operation of the sensor even when heavier hydrocarbons are present.

The composition includes the concentration of methane, ethane, propane, butane isomers (n-butane, iso-butane), pentane isomers (n-pentane, iso-pentane, neo-pentane), hexane isomers (methylpentanes, dimethylbutanes), heptanes, octanes and carbon dioxide gas.

Analysis involves determination of the total concentration and relative ratios of hydrocarbon gases and carbon dioxide in the gas sample. Analysis of the hydrocarbon gases may involve determining concentrations of individual gases and/or combinations of gases.

In order to detect the full concentration range of hydrocarbon gases, the sample gas path length is set such that the primary or strongest absorption band from 3.15 to 3.55 µm is used at low concentrations and once this region starts to saturate the lower absorbance or shoulder regions on either side of the primary band may be used to detect higher concentrations. This reduces the non-linearity within the calibration segments.

The multi-channel spectral data generated by the spectrometer is analysed using multivariate techniques such as partial least squares regression in order to determine the gas concentrations and ratios. The 2.0-5.0 μm spectral range is used as it contains the primary and secondary hydrocarbon absorption band as well as the primary and secondary carbon dioxide absorption bands. This allows different portions of the spectrum to be used based on concentrations and gases being detected.

Figure 7:
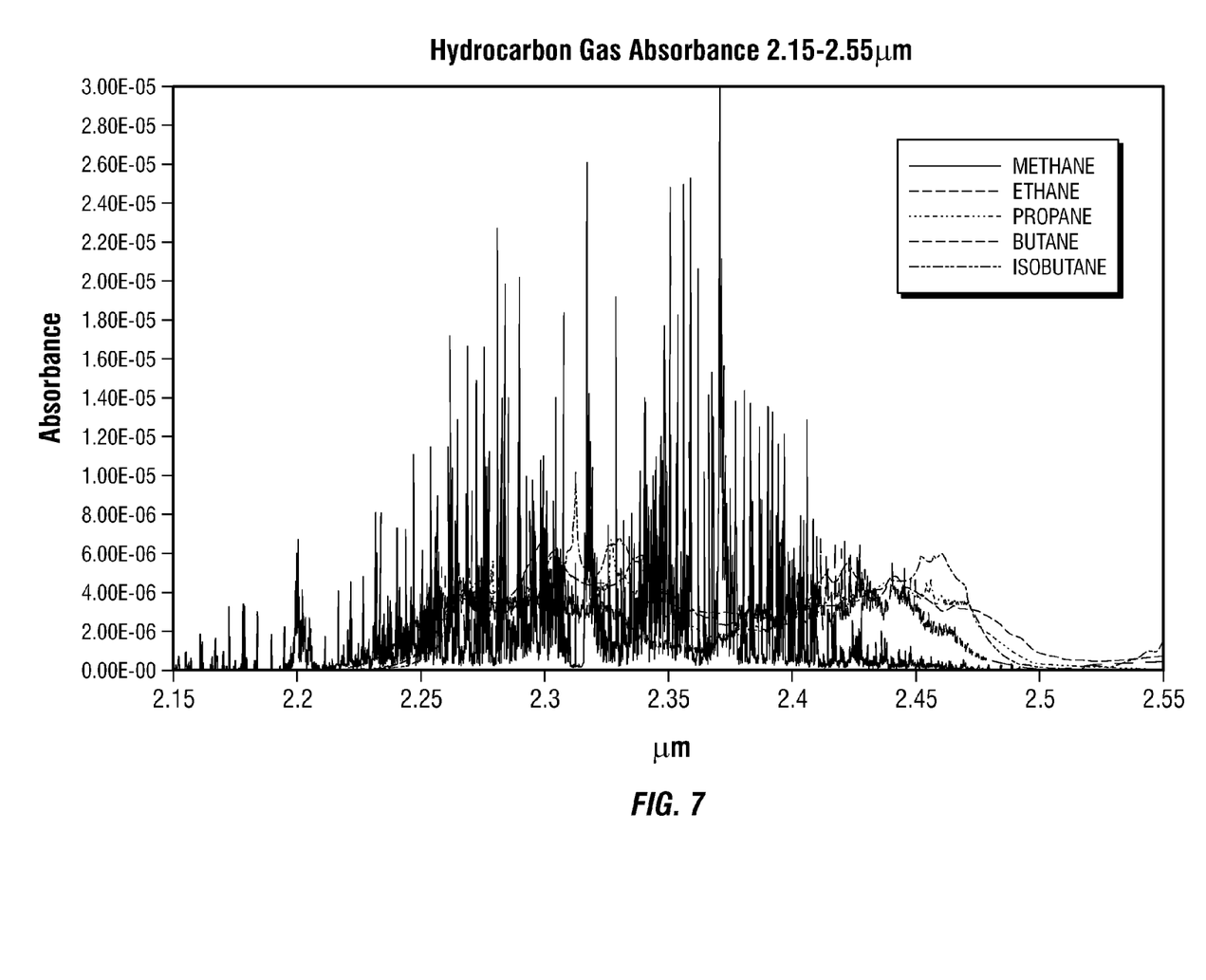
FIG. 7 shows a Spectral Data Chart of the Secondary Hydrocarbon Infrared Absorbance Region 2.15-2.55 µm.

The primary hydrocarbon absorption band is in the 3.15-3.55 μm region of the infrared spectrum as shown in FIG. 4. The lower absorbance shoulder region of the hydrocarbon gases are shown in FIG. 5. The upper absorbance shoulder region of the hydrocarbon gases are shown in FIG. 6. The secondary hydrocarbon absorption band is in the 2.15-2.55 μm region of the Infrared Spectrum as show in FIG. 7. The shoulder and secondary absorption regions feature lower absorbance than the primary band and thus can be utilized for higher concentrations of hydrocarbon gases when the primary absorption band saturates. Once the primary absorption region of the spectrum becomes saturated, the upper and lower shoulder regions and the secondary absorption region can be used. This allows for greater dynamic range in the detection of the HC gases. Specifically to allow a detectable range from tens of ppm total HC gas to close to 100% total HC gas.

Figure 8:
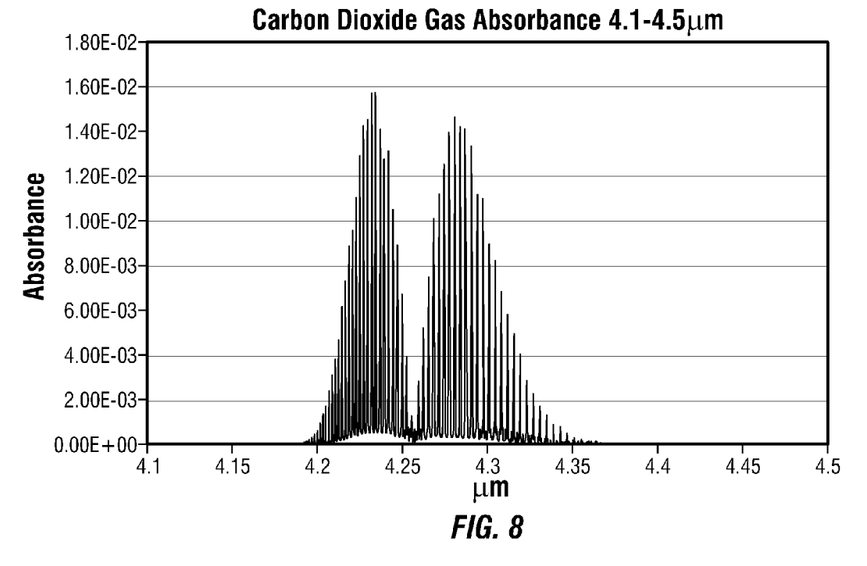
FIG. 8 shows a Spectral Data Chart of the Primary Carbon Dioxide Infrared Absorbance Region 4.1-4.6 µm.
Figure 9:
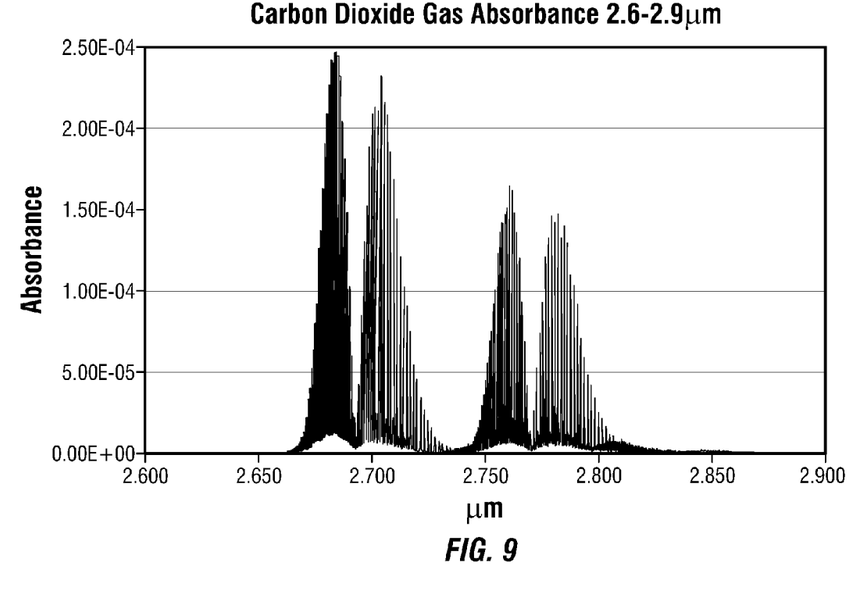
FIG. 9 shows a Spectral Data Chart of the Secondary Carbon Dioxide Infrared Absorbance Region 2.6-2.9 µm

The primary absorption band for carbon dioxide is used for measurement of lower concentrations of carbon dioxide. The primary absorption band for carbon dioxide is in the 4.2-4.4 μm spectral range as shown in FIG. 8. The secondary carbon dioxide absorption band lies in the 2.6-2.8 μm spectral region as shown in FIG. 9. The secondary band features lower absorbance and thus can be utilized for higher concentrations of carbon dioxide when the primary band saturates.

Analysis of the hydrocarbon gases covers a wide concentration range, from less than about 100 ppm to 100 percent of total hydrocarbon gas concentration by volume. Analysis of carbon dioxide concentration covers a range from less than 100 ppm to about 20 percent concentration by volume in the presence of the hydrocarbon gases.

The gas analyzer calculates hydrocarbon and carbon dioxide gas concentrations up to once a second and exports them to the electronic drilling recorder network installed on the drilling rig using the industry standard protocol Wellsite Information Transfer Specification (WITS).

Figure 1:
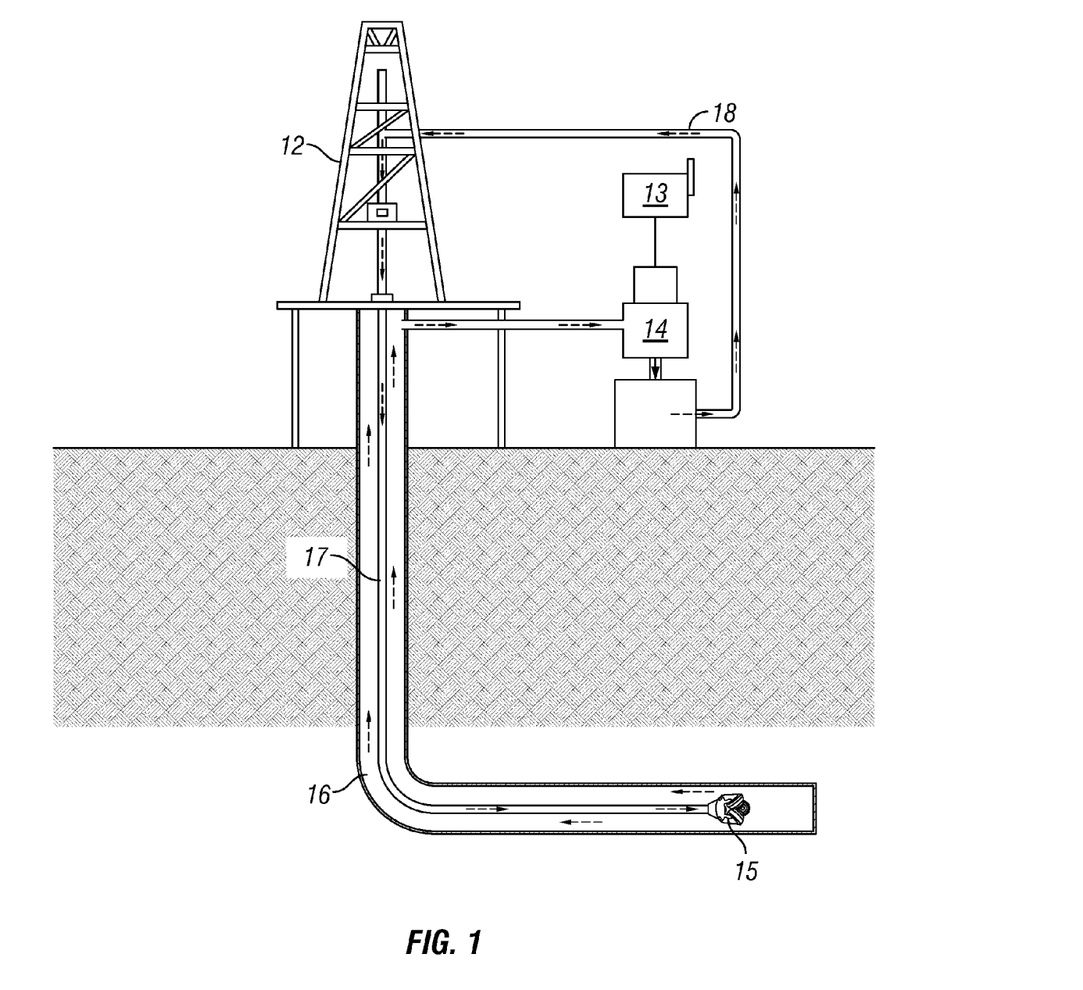
FIG. 1 shows an illustrative arrangement of a block diagram of an Oil and Gas drilling rig site that has on it a gas analyzer according to the invention.
Figure 2:
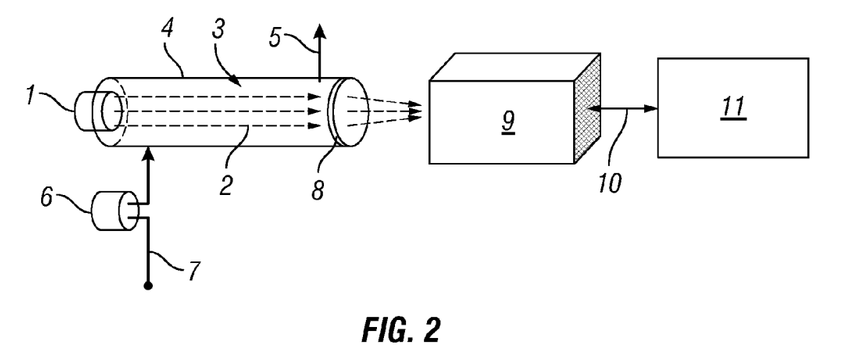
FIG. 2 shows a block diagram of the Gas Analyzer components of FIG. 1.

FIG. 1 shows an oil and gas drilling rig site equipped with a gas analyzer. The oil and gas drilling rig (12) sits atop a drill string (17) having a drill bit (15) attached at its end. The drill string contains the well bore (16). The gas analyzer (13) is attached to and in communication with the gas trap (14). The gas trap sends gaseous samples from the drilling mud (18) and compositional analysis is performed in the analyzer.

Figure 3:
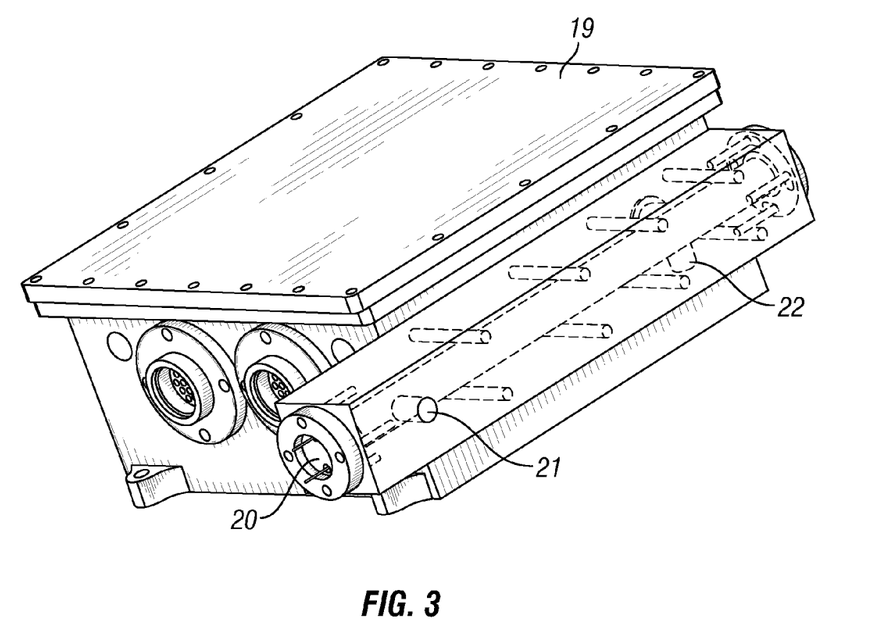
FIG. 3 shows a view of the Hydrocarbon and Carbon Dioxide sensor of the Gas Analyzer of FIG. 1. Infrared spectrometer (19) is attached to an infrared light source (20) and it has a gas sample inlet (22) and a gas sample exhaust (21).

As shown in FIG. 3, the Gas Analyzer System consists of a wide band infrared emitter (1) generating collimated infrared radiation (2) covering the 2 to 5 μm spectrum. The sample gas (3) within the gas cell (4) will absorb the infrared radiation according to the absorption spectrum of the sample gas components. The sample gas pump (6) draws the sample gas from the sample inlet (7) and after passing through the gas cell the sample gas is exhausted at the sample gas outlet (5). A focusing optic element (8) directs the radiation from the gas cell into the spectrometer (9). The spectrometer measures the resulting absorption spectrum of the sample gas consisting of 60 or more spectral channels. The system processor electronics (11) controls the operation of the spectrometer and receives the output spectrum data via a control and communications interface (10). The system processor compares the absorption spectrum of the sample gas to a reference spectrum (a spectrum measured with no absorbing gas present), and it performs the multivariate regression based on the calibration models to generate the sample gas predictions.

Figure 10:
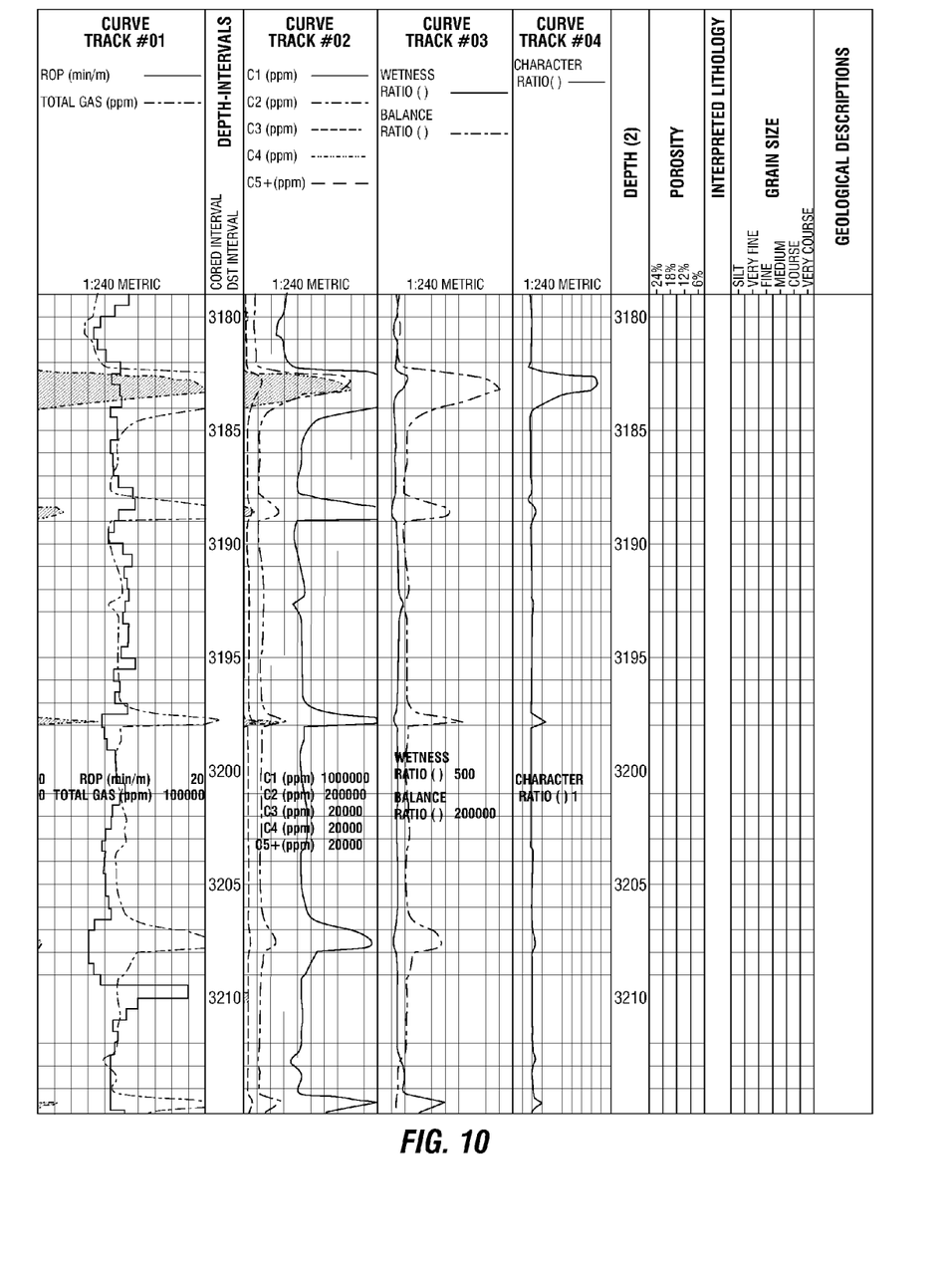
FIG. 10 shows a section of a Geological Striplog displaying the Gas Analyzer Curve Data.
Figure 11:
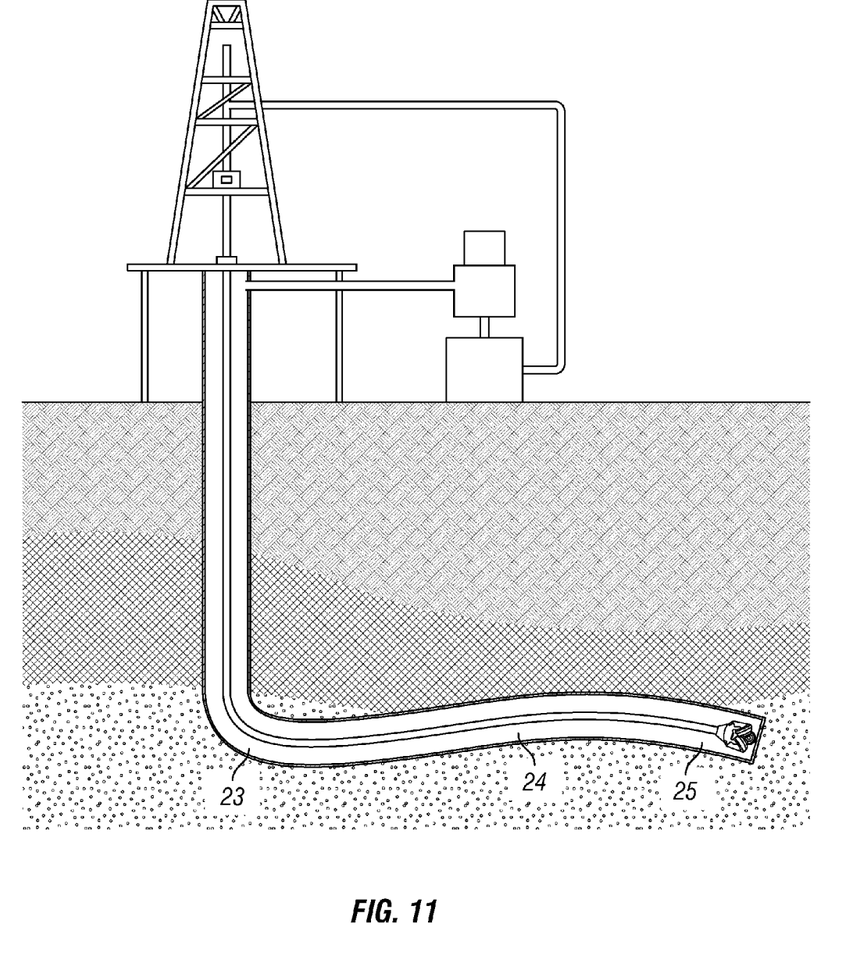
FIG. 11 shows a diagram of a drilling rig drilling a Horizontal Well. Further.

As shown in FIG. 10, Hydrocarbon and Carbon Dioxide data curves are displayed in a geological Striplog. Industry derived Gas Ratio formulas such as Wetness, Balance and Character Ratios are also displayed and used to indicate the changing trends of hydrocarbon state.

The invention claimed is:

1. A device that analyzes the composition of hydrocarbon gases comprising methane, ethane, propane, n-butane, iso-butane, n-pentane, iso-pentane, neo-pentane, hexane isomers, heptane isomers, and octane isomers released from drilling muds, wherein the device comprises a wide band infrared emitter, a gas cell in which the sample gas is irradiated, a Fourier Transform Infrared (FTIR) spectrometer measuring a primary hydrocarbon absorption spectrum of 3.15 to 3.55 μm and primary absorption spectrum shoulder regions of 2.9 to 3.15 μm and 3.5 to 4.2 μm, a focusing optic element that directs gas cell radiation into the spectrometer, and a system processor that performs analysis of the absorption spectrum to determine the gas composition.

2. The device of claim 1 further comprising a non-combustion type detector.

3. The device of claim 1 further comprising a strip recorder.

4. The device of claim 1 wherein the device analyzes hydrocarbon gases comprising one to eight carbons released from drilling muds at least once every 10 seconds.

5. The device of claim 1 further comprising an integrated data communication device for offsite monitoring.

6. The device of claim 1 further comprising the FTIR spectrometer having a spectral resolution of 10 nm or less within the 2.0 to 5.0 μm range.

7. A method of detecting, analyzing and quantifying the composition of hydrocarbon gases liberated from the drilling mud of an oil and/or gas well using multi-channel infrared spectral analysis of the sample gases, the method comprising: (a) liberating gases from drilling mud to form a gas sample; (b) drawing the sample into a gas measurement cell using an electromechanical pump; (c) irradiating the gas sample with infrared radiation from a wide band source; (d) using a Fourier Transform Infrared (FTIR) spectrometer to measure the primary hydrocarbon absorption spectrum of 3.15 to 3.55 μm of the sample gas based on comparison to a reference spectrum, wherein primary hydrocarbon absorption spectrum shoulder regions of 2.9 to 3.15 μm and 3.5 to 4.2 μm and a secondary hydrocarbon absorption spectrum of 2.15 to 2.55 μm are used once the primary hydrocarbon absorption spectrum starts to saturate, in order to extend the hydrocarbon gas detection range up to 100% concentration; (e) using a system processor to perform multivariate analysis of the absorption spectrum allowing the sample gas hydrocarbon composition to be analyzed and quantified, and (f) using multiple calibration models utilizing different spectral regions to increase dynamic range of hydrocarbon gas detection and quantification.

8. The method of claim 7 further comprising simultaneously measuring hydrocarbon gases comprising methane, ethane, propane, n-butane, iso-butane, n-pentane, iso-pentane, neo-pentane, hexane isomers, heptane isomers, and octane isomers present in drilling muds.

9. The method of claim 7 further comprising simultaneously measuring hydrocarbon gases comprising methane, ethane, propane, n-butane, iso-butane, n-pentane, iso-pentane, neo-pentane, hexane isomers, heptane isomers, and octane isomers present in drilling muds in the presence of carbon dioxide.

10. The device of claim 1 further comprising the FTIR spectrometer measuring the secondary hydrocarbon absorption spectrum of 2.15 to 2.55 μm.

11. The method of claim 7 wherein the primary hydrocarbon absorption spectrum of 3.15 to 3.55 μm is used to detect low gas concentrations down to 10 ppm.

* * * * *